(12) United States Patent
Desoyza

(10) Patent No.: US 10,037,667 B2
(45) Date of Patent: Jul. 31, 2018

(54) WRISTBAND AND APPLICATION TO ALLOW ONE PERSON TO MONITOR ANOTHER

(71) Applicant: Erangi Desoyza, Southlake, TX (US)

(72) Inventor: Erangi Desoyza, Southlake, TX (US)

( * ) Notice: Subject to any disclaimer, the term of this patent is extended or adjusted under 35 U.S.C. 154(b) by 0 days.

(21) Appl. No.: 15/206,282

(22) Filed: Jul. 10, 2016

(65) Prior Publication Data

US 2016/0321901 A1 Nov. 3, 2016

Related U.S. Application Data

(63) Continuation of application No. PCT/US2015/026568, filed on Apr. 19, 2015.

(Continued)

(51) Int. Cl.
*G08B 1/08* (2006.01)
*G08B 21/02* (2006.01)
(Continued)

(52) U.S. Cl.
CPC .......... *G08B 21/028* (2013.01); *A61B 5/0022* (2013.01); *A61B 5/0077* (2013.01); *A61B 5/0205* (2013.01); *A61B 5/02438* (2013.01); *A61B 5/11* (2013.01); *A61B 5/1112* (2013.01); *A61B 5/681* (2013.01); *A61B 5/6843* (2013.01); *A61B 5/747* (2013.01);
(Continued)

(58) Field of Classification Search
CPC ............................ G08B 21/04; G08B 21/0446; G08B 21/0247; G08B 21/0216; A61B 5/1118; A61B 5/2055; A61B 5/205; A61B 5/00; A61B 5/11; H04N 7/147; H04N 7/14; G01S 5/0072; G01S 5/12; G01S 5/0284; G01S 5/02
USPC .......... 340/539.11, 573.6, 525, 573.1, 686.1, 340/426.19, 539.32, 539.12, 539.13, 340/539.15; 348/14.02; 455/404.1, 455/404.2, 457, 41.2, 456.1; 600/300; 342/357.34, 357.55, 357.2
See application file for complete search history.

(56) References Cited

U.S. PATENT DOCUMENTS

| | | | | |
|---|---|---|---|---|
| 5,289,163 | A * | 2/1994 | Perez | G08B 21/0247 340/525 |
| 6,246,376 | B1 * | 6/2001 | Bork | G01S 1/047 342/357.34 |

(Continued)

*Primary Examiner* — Hoi Lau

(57) ABSTRACT

According to an embodiment of the disclosure, a wearable device includes a plurality of sensors. The plurality of sensors are configured to detect information concerning a wearer or a surrounding of the wearer of the wearable device. At least some of the detected information is automatically communicated from the wearable device to a remote application based on either a request from a user of the remote application or a trigger initiated on the wearable device when the detected information from the one or more sensors indicate an event has occurred. In certain configurations, the event may be an uttered request for help or a detect increase in heart rate above an expected signature. In certain configurations, some of the information is transmitted to a security or law enforcement agency. In certain configurations, some of the information transmitted is prior recorded information that would otherwise be deleted had the request or trigger not occurred.

16 Claims, 5 Drawing Sheets

Related U.S. Application Data

(60) Provisional application No. 61/982,301, filed on Apr. 21, 2014.

(51) Int. Cl.
*A61B 5/0205* (2006.01)
*A61B 5/00* (2006.01)
*A61B 5/024* (2006.01)
*A61B 5/11* (2006.01)
*G08B 21/04* (2006.01)
*G08B 25/01* (2006.01)
*G08B 29/18* (2006.01)

(52) U.S. Cl.
CPC ..... *G08B 21/0266* (2013.01); *G08B 21/0286* (2013.01); *G08B 21/043* (2013.01); *G08B 21/0446* (2013.01); *G08B 21/0453* (2013.01); *G08B 25/016* (2013.01); *A61B 2503/06* (2013.01); *G08B 21/0294* (2013.01); *G08B 29/188* (2013.01)

(56) References Cited

U.S. PATENT DOCUMENTS

| | | | | |
|---|---|---|---|---|
| 6,529,131 B2* | 3/2003 | Wentworth | ........ | G08B 21/0216 340/573.1 |
| 7,671,763 B1* | 3/2010 | Riffel | .................... | G01S 5/0072 340/426.19 |
| 8,102,316 B1* | 1/2012 | Brucker | .................... | G01S 5/12 342/357.2 |
| 9,002,372 B2* | 4/2015 | Shakespeare | ......... | H04W 64/00 340/539.13 |
| 2003/0032436 A1* | 2/2003 | Mikuni | .................. | G01C 21/20 455/457 |
| 2003/0187336 A1* | 10/2003 | Odagiri | ................. | A61B 5/1118 600/300 |
| 2007/0066323 A1* | 3/2007 | Park | .......................... | G01S 5/02 455/456.2 |
| 2007/0197878 A1* | 8/2007 | Shklarski | ........... | A61B 5/02055 600/300 |
| 2007/0279237 A1* | 12/2007 | Julian | .................... | G01S 5/0284 340/686.1 |
| 2008/0062120 A1* | 3/2008 | Wheeler | .............. | G08B 25/016 345/156 |
| 2008/0266118 A1* | 10/2008 | Pierson | ................ | A61B 5/0205 340/573.6 |
| 2009/0033736 A1* | 2/2009 | Thomason | ............. | H04N 7/147 348/14.02 |
| 2009/0289844 A1* | 11/2009 | Palsgrove | ............ | A01K 15/021 342/357.55 |
| 2011/0210847 A1* | 9/2011 | Howard | ............. | G08B 13/1427 340/539.32 |
| 2011/0228727 A1* | 9/2011 | Julo | ....................... | G01S 19/16 370/328 |
| 2012/0003953 A1* | 1/2012 | Degelsegger | ............ | G08B 7/06 455/404.1 |
| 2012/0088452 A1* | 4/2012 | Jorgensen | ................. | G01S 3/40 455/41.3 |
| 2012/0322380 A1* | 12/2012 | Nannarone | ........ | G08B 13/1427 455/41.2 |
| 2013/0143519 A1* | 6/2013 | Doezema | .......... | G08B 21/0446 455/404.2 |
| 2013/0260785 A1* | 10/2013 | Shakespeare | ......... | H04W 64/00 455/456.1 |
| 2015/0170504 A1* | 6/2015 | Jooste | .................. | A61B 5/6898 340/539.12 |

* cited by examiner

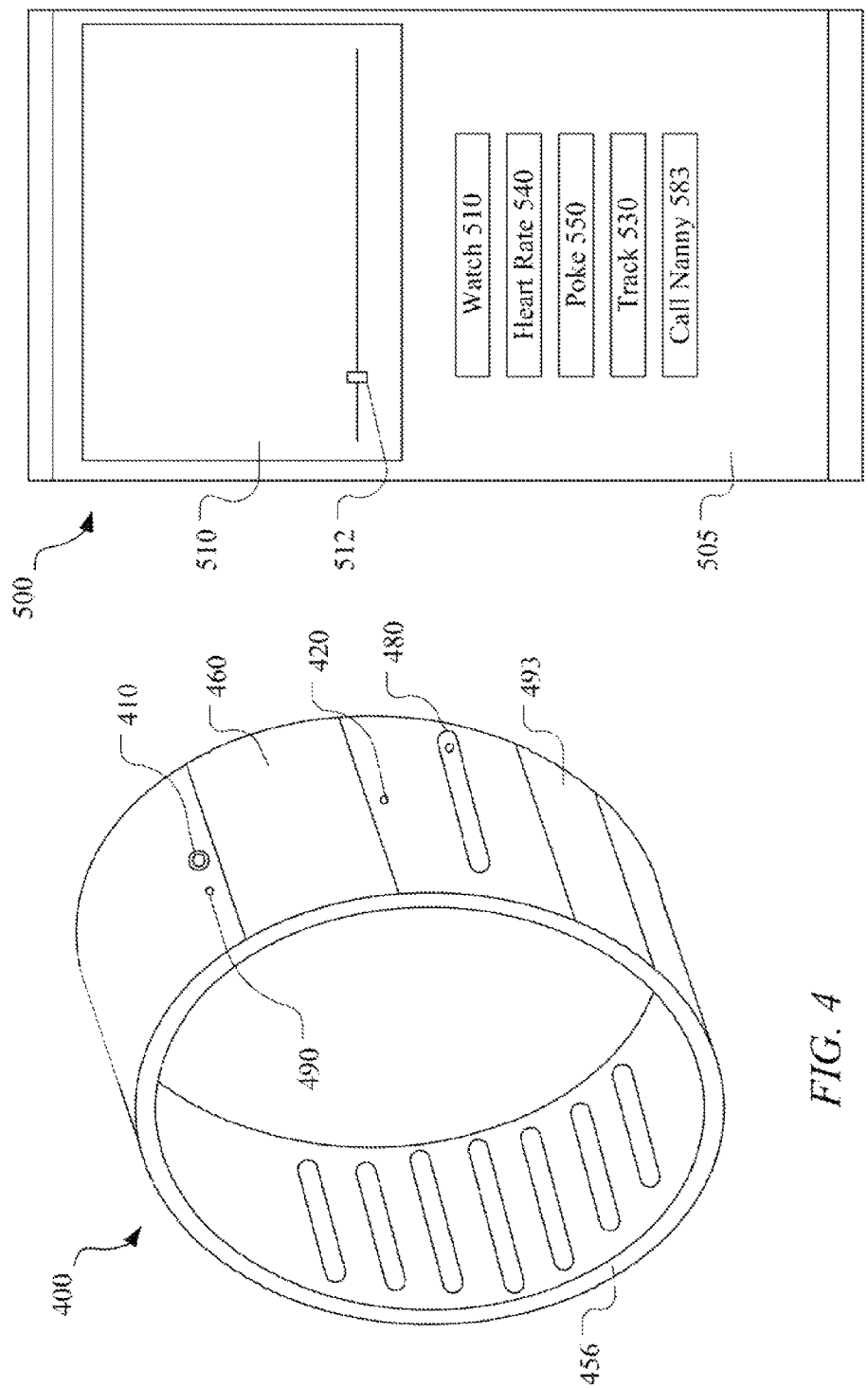

WRISTBAND AND APPLICATION TO ALLOW ONE PERSON TO MONITOR ANOTHER

TECHNICAL FIELD

This disclosure is generally directed to monitoring systems. More specifically, this disclosure is directed to a wristband and application to allow one person to monitor another.

BACKGROUND

There is a great need for families to monitor or "check-in" on their loved ones when they are "away." As non-limiting examples, parents who leave their young children with a babysitter often feel the need to check-in just to make sure everything is all right. Additionally, parents often feel a need to check-in with older children (e.g., including, but not limited to tweens and teens)—also just to make sure everything is going OK. Moreover, adult children feel a need to check in on elderly parents—again to make sure everything is OK.

A conventional mechanism for monitoring loved ones is the use of so-called "nanny cams." However, such nanny cams are stationary and only provide a view of the rooms in which they are mounted. Moreover, such nanny cams do not have the ability to alert others when the loved one is in distress.

SUMMARY OF THE DISCLOSURE

According to an embodiment of the disclosure, a wearable device includes a plurality of sensors. The plurality of sensors are configured to detect information concerning a wearer or a surrounding of the wearer of the wearable device. At least some of the detected information is automatically communicated from the wearable device to a remote application based on either a request from a user of the remote application or a trigger initiated on the wearable device when the detected information from the one or more sensors indicate an event has occurred. In certain configurations, the event may be an uttered request for help or a detect increase in heart rate above an expected signature. In certain configurations, some of the information is transmitted to a security or law enforcement agency. In certain configurations, some of the information transmitted is prior recorded information that would otherwise be deleted had the request or trigger not occurred.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of or the like. The phrase "at least one of," when used with a list of items, means that different combinations of one or more of the listed items may be used, and only one item in the list may be needed. For example, "at least one of: A, B, and C" includes any of the following combinations: A; B; C; A and B; A and C; B and C; and A and B and C. Definitions for certain words and phrases are provided throughout this patent document, those of ordinary skill in the art should understand that in many if not most instances, such definitions apply to prior, as well as future uses of such defined words and phrases.

BRIEF DESCRIPTION OF THE DRAWINGS

For a more complete understanding of this disclosure and its features, reference is now made to the following description, taken in conjunction with the accompanying drawings, in which:

FIG. 4 is an isometric view of a wristband 400, according to an embodiment of the disclosure;

FIG. 5 shows a non-limiting example of a device in which an application may be executed according to an embodiment of the disclosure;

DETAILED DESCRIPTION

Figure 1:
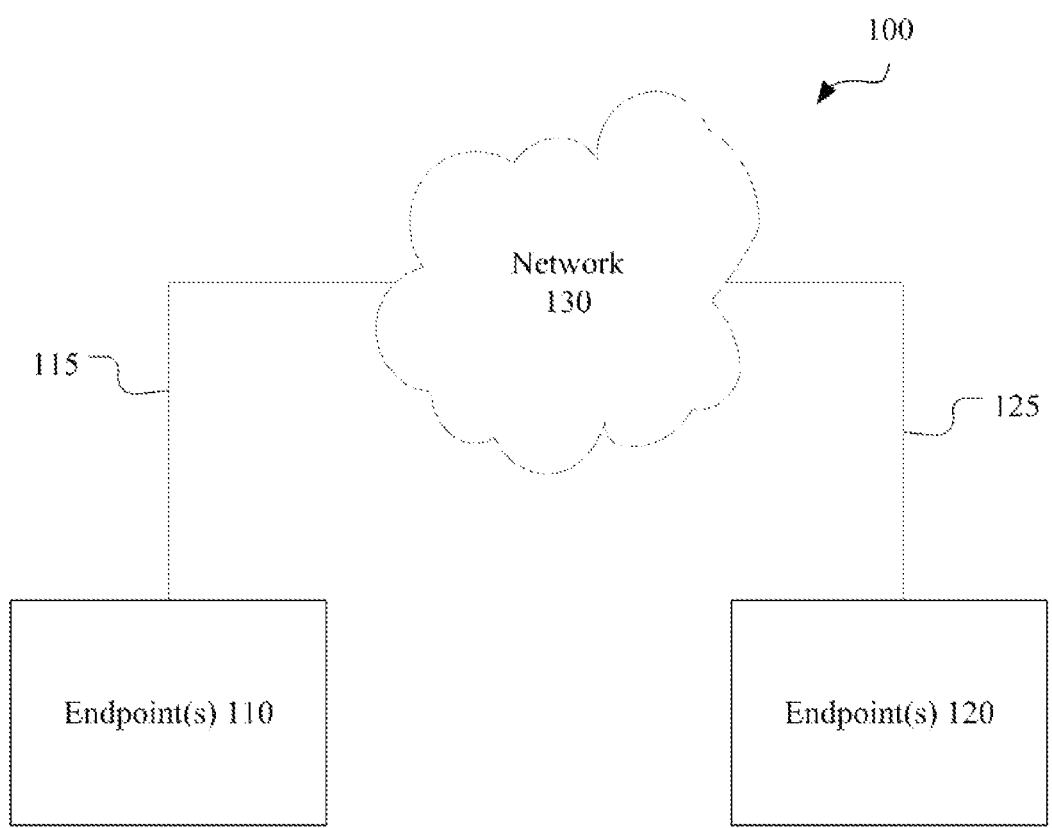
FIG. 1 is a simplified block diagram illustrative of a communication system 100 that can be utilized to facilitate communication between endpoint(s) through a communication network, according to particular embodiments of the disclosure.

The FIGURES described below, and the various embodiments used to describe the principles of the present disclosure in this patent document are by way of illustration only and should not be construed in any way to limit the scope of the disclosure. Those skilled in the art will understand that the principles of the present disclosure invention may be implemented in any type of suitably arranged device or system. Additionally, the drawings are not necessarily drawn to scale.

Recognizing the above-described concerns in the background, certain embodiments of the disclosure provide a solution whereby a portable video/audio monitoring device is worn by an individual being monitored. In certain configurations, the wearable device has geolocation capabilities. Additionally, in certain configurations, the wearable device has a variety of sensors to monitor the individual. The wearable device communicates with a remote device (which, for example, may be an application on a smart phone) to provide a variety of information about the monitored individual—including, for example, alerts and audio/visual information. Such a system will help families stay connected with and/or bond with their loved ones more effectively.

This system brings childcare into the current generation by allowing parents to bond with their children at any moment that they choose. In a particular configuration, the system includes a wearable device with an on demand live video/audio capability that is worn on the wrist of the individual being monitored. This device wirelessly communicates with a smart phone based software application that is in the hands of the person who is doing the monitoring. In certain configurations, the software application will allow the individual who is monitoring to push a button, which triggers the device to automatically communicate information allowing the user to wirelessly see and hear their loved ones movements and whereabouts. In particular embodiments, in such a configuration and unlike a scenario where one answers a mobile phone (or responsively sends a text), information is automatically transmitted. As described below, in other configurations, the wearer of the device may be allowed to selectively send information. Additionally, in certain configurations, the wearable device includes a heart rate monitor sensor that can report heart rate information to the software application, for example, to allow the person with the smart phone to view such information. The heart rate sensor also can be used in conjunctions with alert triggers that indicate distress. For example, when the heart rate exceeds a trigger threshold, an alert can be sent out to cause a variety of actions that will be discussed below (e.g., recording of audio/visual information)—in addition to notifying the smart phone application.

Additionally, audio sensors can also triggers alerts, further causing actions on the smart phone. For example, when crying is detected the alert can be triggered. Moreover, when spoken words are iterated (e.g., "help"), the trigger can be activated and appropriate actions (e.g., recording of audio/visual information) and alerts can occur. Along with this, when the subjects heart rate goes above a certain level (e.g., indicating a sudden increase due to distress and/or crying) an automatic alert will sound. As described below, this and other configurations can compare information detected from sensors to threshold signatures to see if an event is occurring, requiring an alert or action as opposed to a scenario that does not require an alert or action. In particular configurations, a user can configure the sensitivity of thresholds to receive more or less alerts.

In a particular configuration, the wearable device may be worn on the wrist as a wristband. If the wristband is taken off or cut off, an alert will be sent to the smart phone, triggering, for example, a sound—in addition to other potential actions. In certain configurations, this will be determined by pulse rate or lack thereof. Particular configurations will have different sizes and colors for different age groups and people. In particular configurations, the device can be detached from the wristband and be recharged. In particular configurations, the wrist band will be soft, pliable and waterproof. In particular configurations, multiple sized wristbands that can be sold separately.

FIG. 1 is a simplified block diagram illustrative of a communication system 100 that can be utilized to facilitate communication between endpoint(s) 110 and endpoint(s) 120 through a communication network 130, according to particular embodiments of the disclosure. As used herein, "endpoint" may generally refer to any object, device, software, or any combination of the preceding that is generally operable to communicate with and/or send information to another endpoint. In certain configurations, the endpoint(s) may represent a user, which in turn may refer to a user profile representing a person. The user profile may comprise, for example, a string of characters, a user name, a passcode, other user information, or any combination of the preceding. Additionally, the endpoint(s) may represent a device that comprises any hardware, software, firmware, or combination thereof operable to communicate through the communication network 130.

Examples of an endpoint(s) include, but are not necessarily limited to, a computer or computers (including servers, applications servers, enterprise servers, desktop computers, laptops, netbooks, tablet computers (e.g., IPAD), a switch, mobile phones (e.g., including IPHONE and Android-based phones), networked televisions, networked watches, networked glasses, networked disc players, components in a cloud-computing network, or any other device or component of such device suitable for communicating information to and from the communication network 130. Endpoints may support Internet Protocol (IP) or other suitable communication protocols. In particular configurations, endpoints may additionally include a medium access control (MAC) and a physical layer (PHY) interface that conforms to IEEE 801.11. If the endpoint is a device, the device may have a device identifier such as the MAC address and may have a device profile that describes the device. In certain configurations, where the endpoint represents a device, such device may have a variety of applications or "apps" that can selectively communicate with certain other endpoints upon being activated.

The communication network 130 and links 115, 125 to the communication network 130 may include, but is not limited to, a public or private data network; a local area network (LAN); a metropolitan area network (MAN); a wide area network (WAN); a wireline or wireless network (WIFI, GSM, CDMA, LTE, WIMAX, BLUETOOTH or the like); a local, regional, or global communication network; portions of a cloud-computing network; a communication bus for components in a system; an optical network; a satellite network; an enterprise intranet; other suitable communication links; or any combination of the preceding. Yet additional methods of communications will become apparent to one of ordinary skill in the art after having read this specification. In particular configuration, information communicated between one endpoint and another may be communicated through a heterogeneous path using different types of communications. Additionally, certain information may travel from one endpoint to one or more intermediate endpoint before being relayed to a final endpoint. During such routing, select portions of the information may not be further routed. Additionally, an intermediate endpoint may add additional information.

Although endpoint generally appears as being in a single location, the endpoint(s) may be geographically dispersed, for example, in cloud computing scenarios. In such cloud computing scenarios, and endpoint may shift hardware during back up. As used in this document, "each" may refer to each member of a set or each member of a subset of a set.

When the endpoints(s) 110, 130 communicate with one another, any of a variety of security schemes scheme may be utilized. As an example, in particular embodiments, endpoint(s) 120 may represent a client and endpoint(s) 130 may represent a server in client-server architecture. The server and/or servers may host a website. And, the website may have a registration process whereby the user establishes a username and password to authenticate or log in to the website. The website may additionally utilize a web application for any particular application or feature that may need to be served up to website for use by the user.

A variety of embodiments disclosed herein may avail from the above-referenced communication system or other communication systems.

Figures 2, 3:
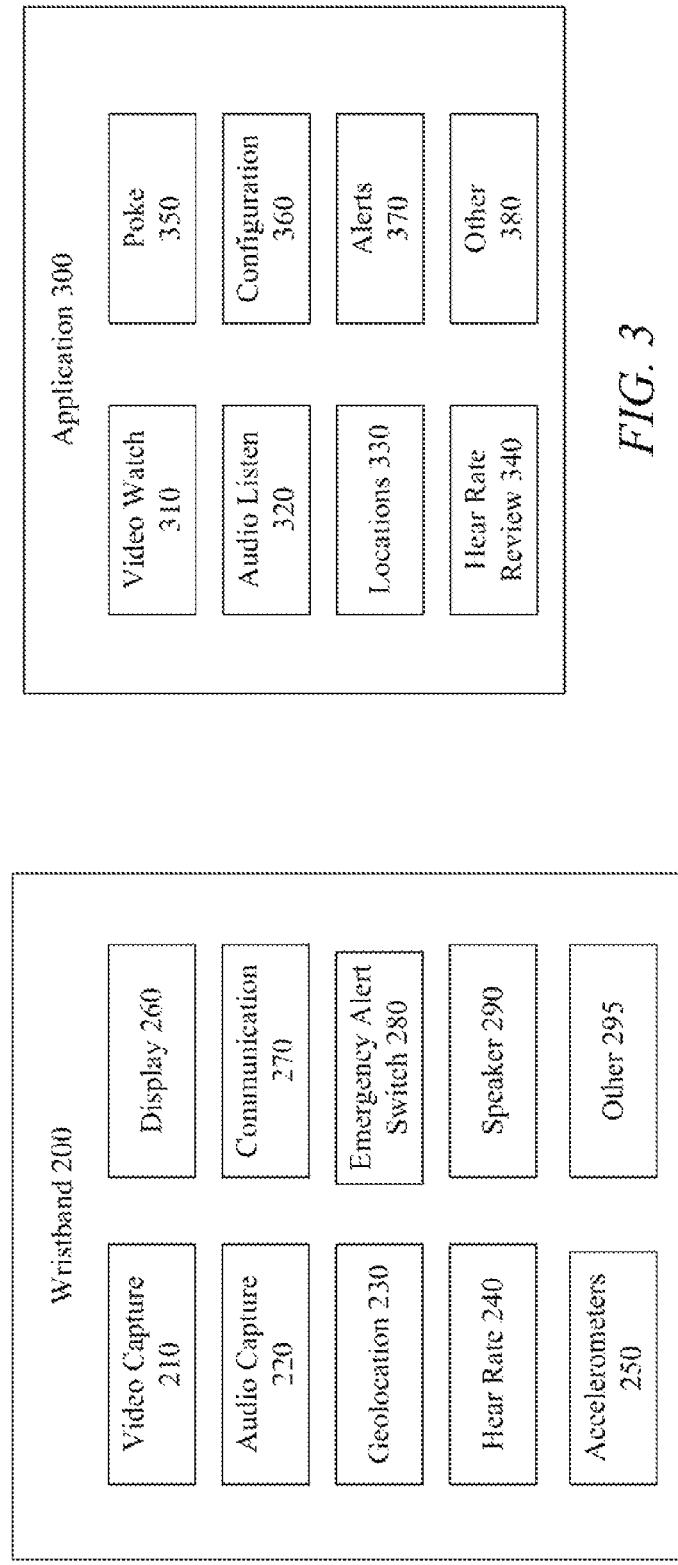
FIG. 2 illustrates components of a wristband, according to an embodiment of the disclosure.
FIG. 3 illustrates non-liming example of components that may be utilized in an application, according to an embodiment of the disclosure.

FIG. 2 illustrates components of a wristband 200, according to an embodiment of the disclosure. In FIG. 2, the wristband 200 is shown with the following non-limiting components: a video capture component 210, an audio capture component, 220, a geolocation component 230, a heart rate component 240, an accelerometers component 250, a display component 260, a communications component 270, an emergency alert component 280, a speakers component 290, and an other sensory component 295. For purposes of brevity, other components have not been described (e.g., communication bus between components, processors, memory, and the like); however, one of ordinary skill in the art will recognize the operation of such other components. For example, the wristband may utilize components described with reference to FIG. 8. Additionally, although certain components will be described with reference to FIG. 2, other configurations applying teachings of the disclosure may have more, less or different components.

The video capture component 210 is generally configured to capture video of a surrounding of the wristband 200. In particular configurations, the video capture component 210 can be remotely activated, for example, using the application described with reference to FIG. 3. In other configurations, the video capture component 210 can be activated based on logical outputs received from other components. As a non-limiting example, where the combination of outputs from one or more of the audio capture, accelerometers, and heart rate components suggest that an event is occurring, the video capture component can activate recording and stream to a location, for example, a server in a cloud. The location to which the video is streamed may temporarily store data until a viewer using the application of FIG. 3 is able to review the recorded information. Upon viewing, the user may be able to watch real-time or rewind to watch a time closer to when the actual event occurred. In particular configurations, the video capture component may store captured data locally in the wristband 200 for a temporary period of time, dumping data older than a predetermined amount (e.g., 30, 60, or 90 seconds). In particular configurations, the older data may be preserved and uploaded for a predetermined time before the event. For example, if the buffer is ninety seconds and an event occurs, the prior ninety seconds can be preserved and uploaded upon detection of an event. Such a configuration may allow a viewer to determine what happened prior to an event, causing a trigger. Additional details of modifications to the video capture component 210 are described below with reference to FIGS. 6A and 6B.

The audio capture component 220 in a manner similar to the video component is generally configured to capture the audio of a surrounding of the wristband 200. As introduced above, in particular configurations a voice command captured by the audio captures component 220 may initiate an action. To register such voice commands, any suitable voice signature recognition technique may be utilized. For example, where the word is the utterance of "help" by a child, multiple recitations of the child saying "help" may be prerecorded to determine a signature and associated tolerances for the signature. Such a signature review may assist in detecting the utterance by wearer or the device as opposed to an utterance of the same words by a non-wearer of the device. In addition to comparing the signature of the utterance of the word help, a broader signature can also be reviewed to see if the output of the other sensors are consistent with someone actually stating help. For example, heart rate may expected to be increased with the utterance of help.

The geolocation component 230 is any suitable component for determining the location of the wristband 200. Non-limiting examples include cell-tower triangulation, global positioning system triangulation, and Wi-Fi triangulation, or combinations of the preceding. Methods of determination may either involve propagated signals being interpreted by the geolocation component 230 (e.g., GPS) or the geolocation component 230 transmitting a beacon signal that is captured by more than one receiver (e.g., uplink time of arrival). Thus, the geolocation may be determined by the wristband 200 in certain configurations and other devices in other configurations. Additionally, more than one geolocation technique may be utilized. Additionally, other suitable geolocation techniques will become apparent to one of ordinary skill in the art. In particular configurations, a determined geolocation can be communicated, for example, to allow the application 300 of FIG. 3 to see the location of the wristband.

The heart rate component 240 determines the heart rate of the wearer of the wristband 200 using any suitable sensor. This information may be continuously or selectively communicated to the application 300 device. In particular configurations, the output of the heart rate sensor may be utilized to trigger or activate other components. For example, an increased heart rate above and beyond a normal expected heart rate may suggest that the wearer is frightened. Accordingly, an alert may be sent to the application 300 or a phone. In particular configurations, the heart rate component 240 may determine an expected heart rate pattern based on outputs from other components. For example, the geolocation and accelerometers may suggest that the location and increase in hear rate is expected because, for example, the wearer is at recess during a scheduled time for recess. In particular configurations, an output for the heart rate component 240 can be stored at a remote server, for example, in the cloud for subsequent analysis by an engine in the cloud. Stated differently, the signatures and/or thresholds may be dynamically updated based on the data captured by the wearable device. The wearable device learns what is to be expected. In particular configurations, threshold can also be customized to yield more or less frequent alerts.

In certain configurations, the heartbeat is used to determine whether or nor the wristband 200 is still attached to the wearer. Where the heartbeat is not detected for a predetermined time, the hear rate component 240 may signal an alert that the wristband 200 has been removed. Additionally, the heart rate component 240 may recognize the specific heart rate and pulse characteristics (signature) of a particular wearer. Accordingly, one trying to trick the wristband by removing it and quickly placing on another wrist will not be successful.

The registering of a signature of the heart beating signature may be determined over time by analyzing how the particular wearer's heart beats.

Although this anti-removal mechanism is described, other anti-removal mechanisms may be utilized according to other configurations. For example, in one configuration, a temperature of the body may be measured and, if too low, a removal may be detected. In another configuration, an electrical signal may be sent from the wristband 200 through the body of the wearer (using the body as a circuit) and back to the wristband 200. Where this signal is communicated, but not received, a removal event may be detected. Any suitable alert may be communicated when removal is detected.

The accelerometers component 250 measure accelerative phenomena using multiple accelerometers. Such an accelerometer component 250 can provide information on movement of the wearer 250. This movement information may be utilized in particular configurations for determining whether an event occurs. For example, where the gravity on the accelerometers is detected as moving in a rolling pattern accompanied by a crying sound and/or erratic detection by the camera, an event of someone falling may be detected.

The display component 260 may include any of a variety of features to allow the wearer of the wristband 200 to receive visual feedback. Depending on the age of the person wearing the wristband 200, the display component 260 may take on a variety of configurations. In particular configurations, the display component 260 may contain a digital readout of time—emulating a watch. In other configurations, the display component 260 may contain a screen that is enabled to display text messages or other electronic messages, for example, to allow a parent or other person to update the wearer of the wristband 200 on information (e.g., "I will pick you up by the side entrance of the movie theater."). In other configurations, the display component 260 may contain a display that allows viewing of a video, for example, to entertain a child. The video may be pushed or streamed to the wristband 200 over the network.

The communication component 270 provides any appropriate communication the wristband 200 may need for communication with other devices. For example, the communications component 270 may allow communication via one or more of the communication techniques described with reference to FIG. 1. As a non-limiting recapitulation of certain communication techniques, the communication component may communicate using protocols for Wi-Fi, cell-tower, and blue-tooth communications.

The emergency alert switch 280 may include any suitable mechanism in which a user can push a button or move a switch to activate pre-programmed alerts. Non-limiting example may include call or texting pre-programmed numbers (e.g., including 911) or alerting the application 300. In particular configurations, the alerting may use a smart calling configuration whereby multiple devices and/or applications are alerted one after another. The information provided in the alert may vary; however, in particular configurations a geolocation along with a saved buffered of audio/video may be immediately transmitted, for example, to the application 300 or another device. In particular configurations, the emergency alert switch 280 may have a "watch me" feature where a wearer of the device is feeling unsafe and needs heightened attention. When the watch me feature is activated, the video and audio capture components 210, 220 may begin recording and the geolocation information can be transmitted to predetermined locations. In particular configurations, any of the information described herein may be communicated to a security or law enforcement agency.

The speaker component 290 may include any of a variety of features to allow the wearer of the wristband 200 to receive audio sounds. For example, the speaker component 290 may display soothing sounds from a parent when an alert is received. Additionally, in particular configurations, the speaker component 290 may provide audio messages left for the wearer. In particular configurations, two-way communications may be established between the wristband 200 and the application 300, for example, providing audio alone, or video and audio.

The other component 295 may include a variety of other items. As described above, temperature may be measured. Additionally, the communication of a signal through the human body may be measured. In yet other configurations, the other component 295 may include a vibration mechanism. In particular configurations, this vibration may be on command, for example, when a user of the smart phone application "pokes" the wristband 200 to elicit a response from the wearer of the wristband as described below.

FIG. 3 illustrates non-liming example of components that may be utilized in an application 300, according to an embodiment of the disclosure. In particular configurations, the application 300 may be a smart phone application used on an IPHONE or ANDROID telephone. However, the application 300 may also be utilized on other devices, including smart watches. Additionally, in certain configurations, components may be accessed on an application 300 on one device (e.g., a laptop, a tablet, or a desktop computer) and synchronized or updated with the application 300 on another device (e.g., a mobile device such as a smart phone or a smart watch).

The non-limiting examples of components in FIG. 3 include a video watch component 310, an audio listen component 320, a location component 330, a heart rate review component 340, a configuration component 360, an alerts component 370, and a general other component 380. Although such components are shown in FIG. 3, other configurations may include more, fewer, or different components.

The video watch component 310 and audio listen component 320 allows the viewer of the application 300 to activate and watch or listen (or both) to what is respectively being captured by the video capture component 210 and the audio capture component 220. As a non-limiting example, when the parent is leaving (e.g., going out to dinner) they are able to activate a "watch" mode or a "listen mode" (or both) by simple pushing a button on their application. This turns on video/audio capabilities. To turn off such functionality, the parent may simply push the "off" button. In particular configuration, the video watch component 310 and/or audio capture component 320 may also enable and disable a recording of what is being captured by each respective component. Further details of one configuration of the video watch component 310 is described with reference to FIGS. 6A and 6B.

The location component 330 may allow the user of the application to locate current and historical location of the wearer of the wristband 200, for example, as a result of the corresponding geolocation component 230. As reference, supra, the geolocation component 230 may either communicate a signal that is used to determine location or may received signals to determine a location. In particular applications, a blue print of the home can be uploaded and displayed with the smart phone application to allow a parent to know exact location of a child with respect to such a blue print. Any suitable technique may be utilized for uploading such a blueprint. The location component 330 may also allow geolocation fences to be created with an alert or reporting of when the wristband 200 crosses such a fence. In particular configurations, a combination of the components (e.g., 310, 320) may be displayed together. For example, the audio and video component viewing may be activated when a wearer of the wearable device crosses a digital fence.

In particular configurations, the locations component 330 may additionally determine if the wristband 200 has wandered two far away from a device executing the application 300. For example, where a parent (having a smart phone with the application 300) and a child (wearing the wristband 200) are in a mall, an alert can be initiated when a predetermined distance has been exceeded. In such a configurations, each respective device may communicate directly with one another—measuring the time difference between receipts of two or more propagated signals (with knowledge of the time between them are communicated). Alternatively, each respective device may be geolocated using techniques recognized by one of ordinary skill in the art.

In particular configurations, when one is alerted that predetermined distance has been exceeded, a compass graphic can be displayed on the application 300 guiding the user of the application 30 to the wristband 200.

The heart rate review component 340 may allow the user of the application 300 to review current and historical heart rates of the wearer of the wristband 200.

The poke component 350 may initiate any suitable mechanism on the wristband 200 to elicit feedback from the wearer. As a non-limiting example, the poke component 350 may initiate a vibration on the wristband 200 (e.g., using the vibration mechanism referenced in the other component 295)—making the wearer look at the wristband. The poke component 350 may initiate other suitable actions on the wristband 200, for example, the video watch component 310 in order to allow the viewer of the application 300 to see the response to the poke The configuration component 360 generally represents any of variety of configurations that may be modified. Non-limiting examples include who and through what contact mechanism (e.g., phone, text, email, smart phone alert) a user is notified of an alert from the wristband 200, the thresholds for alerts, digital fences, and the like. As described above, on may also setup a security or law enforcement agency to receive information. In particular configurations, different settings may be set for different alerts. For example, certain alerts representing less distress may be sent to a first party whereas other alerts representing more distress may be sent to a combination of parties, for example, including the security or law enforcement agency.

The alerts component 370 is a historical listing of alerts that have been activated along with any suitable information, for example, the data captured and stored (e.g., on a cloud).

The general other components 380 allows for other components one of ordinary skill in the art may utilize for functions described herein.

FIG. 4 is an isometric view of a wristband 400, according to an embodiment of the disclosure. The wristband 400 may include components described with reference to FIG. 2 or have other components. The select components shown in this wristband 400 are a video camera 410, a microphone 420, a band 456, a display 460, an emergency alert switch 480, a speaker 490, and a removable power supply 493. Other components (not shown) may also be contained within the wristband 400.

In particular configurations, the band 456 may be made of a flexible material and have ridges as appropriate (and made of the same or different material) to prevent sliding around a wrist. The removable power supply 493 may be a rechargeable battery that can be removed and resupplied to refresh the power supply.

The emergency alert switch 480 is shown as having a button that must be slide in a particular direction before it can be pushed to be activated. Other configurations of the emergency alert switch may be utilized in other embodiments.

FIG. 5 shows a non-limiting example of a device in which an application 500 may be executed according to an embodiment of the disclosure. Although a particular device is shown, it should be understood that other devices may avail from the teachings of the disclosure. The application 500 of FIG. 5, which is shown as being executed on a smart phone, may include components different of similar to those described with reference to FIG. 3. A variety of items are being shown on the display 505 of the smart phone. For example, a video 510 is being shown. In particular configurations, the video may be live. In other configurations, the video may have portions that are recorded. Thus, for example, when an alert occurs, one viewing a live feed may simply move the slider bar to the left to determine what previously happened to trigger the event.

The following non-limiting example buttons are also shown: watch 510, heart rate 540, poke 550, track 530, and call nanny 583. Yet other buttons may be utilized consistent with the teachings of this disclosure. As an example, as will be described blow, controls may be used to move movable cameras on the wearable device. The call nanny button 583 is a short cut to call a preprogrammed number. The functionality of the other buttons should become apparent with the above disclosure. The poke button 500 may elicit any configurable feedback desired. In particular configurations, it may be a simple request for the wearer of the device to look at the device. In addition to the above, a check-in feature may be programmed into the wearable device where certain events are expected to occur at programmed intervals. If the appropriate response is not received for one or more periods, an alert can be generated and sent to the remote monitoring application.

Figure 6:
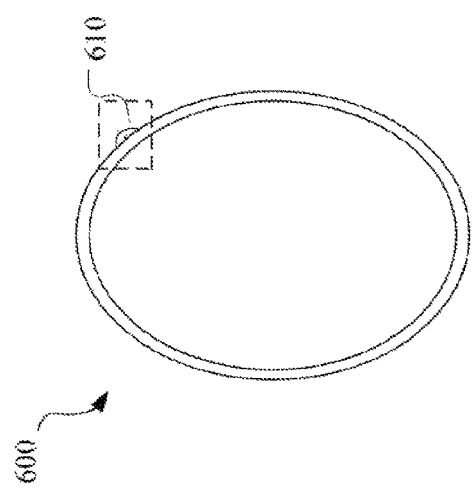
FIGS. 6 and 7 shown details of a camera system on a wristband, according to an embodiment of the disclosure.
Figure 7:
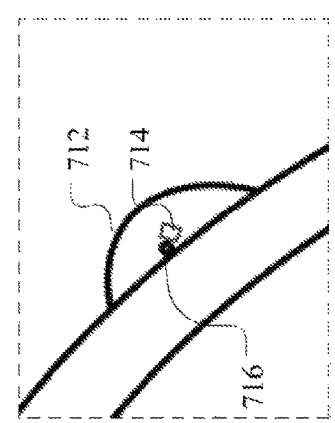

FIGS. 6 and 7 shown details of a camera system 610 on a wristband 600, according to an embodiment of the disclosure. The wristband 600 includes a camera system 610. FIG. 7 details the dotted area of FIG. 6. The camera system 610 includes a camera 714 mounted to a movable configuration 716. A protective dome 712 covers both the camera 714 and movable configuration 716. The movable configuration 716 allows the camera 714 to move in variety of directions to get a better view of a particular area. The movable configuration 716 in particular configuration may be a microelectromechanical system (MEMS). Other suitable mechanisms may also be utilized. Such mechanisms may allow multiple degrees of freedom for movement of the camera. For example, with reference to the surface of the wristband, the movable configuration can allow rotation about a z-axis as well as movement in the x and y-axis, which is three degrees of freedom. In other configurations, movement in the z-axis may be allowed as well as rotation in the x and y-axis.

In particular configurations, the accelerometers 250 (described with reference to FIG. 2) may inform the camera 714 of proper orientation.

Although one camera has been shown above, other configurations may utilize multiple cameras. In certain of such other configurations, the field of view from such fields of view of such multiple cameras may be merged together. In others, they may not be merged. When such multiple cameras are utilized, the accelerometers 250 may provide information as to which camera is expected to have the best view (e.g., based on the measured accelerative phenomena).

Figure 8:
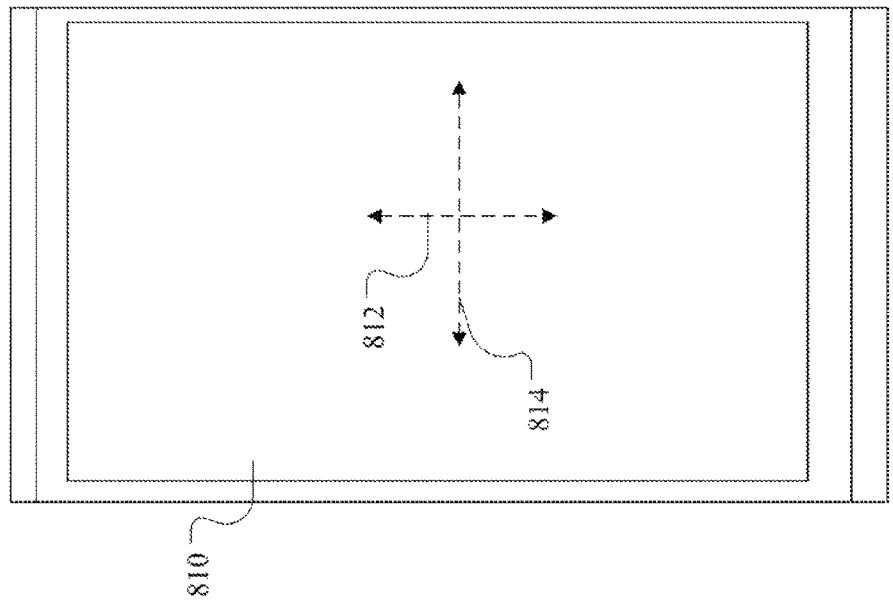
FIG. 8 is an example of a user of an application on the smart phone controlling the direction of the camera of FIG. 7.

FIG. 8 is an example of a user of an application on the smart phone controlling the direction of the camera 714 of FIG. 7. The live video 810 is shown. The direction the camera is facing can be moved, for example, by a user, for example, swiping across the video (as indicated by dashed lines 812, 814). The camera 714 can be moved in other manners as will become apparent to one of ordinary skill in the art reviewing this specification.

In particular configurations, the devices described herein may allow a parent to bond with the child/individual wearing the wristband. Stated differently, the wristband may be used as a device that will allow the caregiver to be able to connect with the wearer at any time. The wristband is versatile enough such that it can be used for babies, children, elderly and anyone in between (e.g., tweens). From the perspective of a child/nanny situation, the wristband takes the place of the previous stationary nanny cams available. This allows for constant visual/audio feedback on child and their whereabouts as well as GPS capabilities. In the case of tween's and elderly, once again the parent/caregiver is able to connect with the individual at all times. An added feature is that the wearer of the wristband is able to alert caregiver in an emergency situation as well. Guardians will be alerted to any signs of distress (e.g., screams, key words, increase or decrease it heart rate, etc.). Also, a switch type button on the wristband utilized by the wearer in the case of older children or elders can alert parent/guardian or video monitoring services/911 if needed in an emergency situation.

Although described as an application generally monitoring a wristband, in particular configurations the application may monitor more than one wristband. In such a configuration, unique identification information is used for each wristband. Additionally, the application may be allowed to switch from information displaying one wristband to the next.

Figure 9:
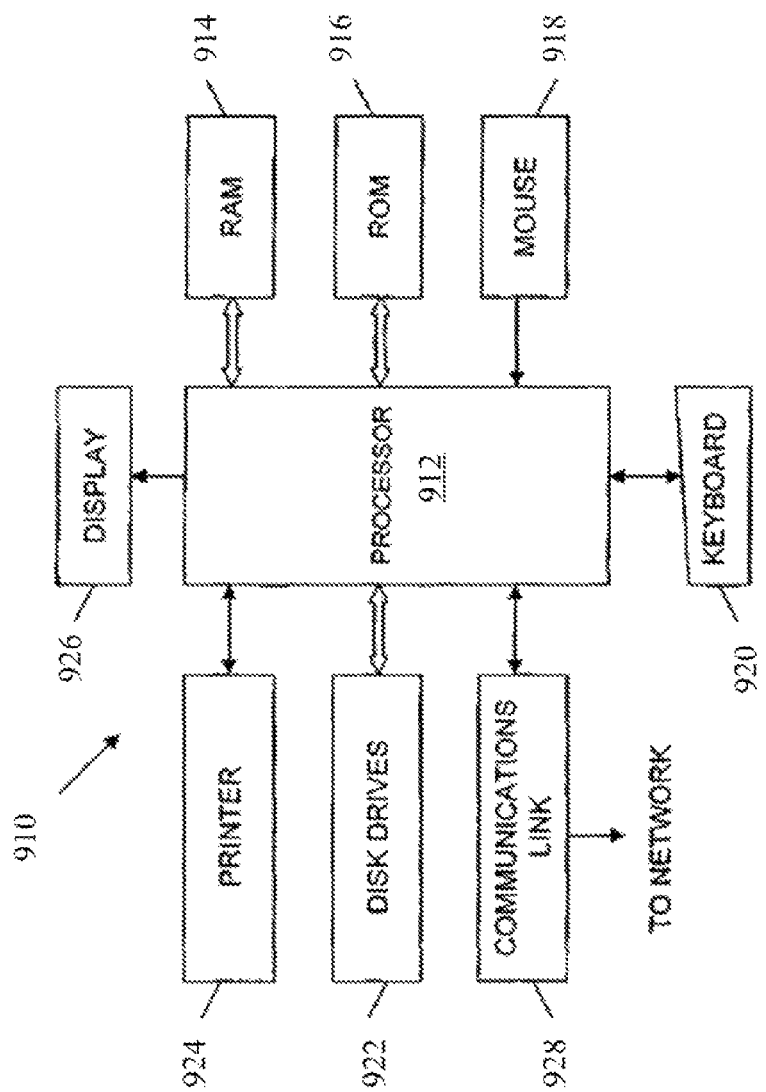
FIG. 9 is an embodiment of a general purpose computer that may be used in connection with other embodiments of the disclosure to carry out any of the above-referenced functions and/or serve as a computing device for endpoint(s).

FIG. 9 is an embodiment of a general purpose computer 910 that may be used in connection with other embodiments of the disclosure to carry out any of the above-referenced functions and/or serve as a computing device for endpoint(s) 110 and endpoint(s) 120. General purpose computer 910 may generally be adapted to execute any of the known OS2, UNIX, Mac-OS, Linux, Android and/or Windows Operating Systems or other operating systems. The general purpose computer 910 in this embodiment includes a processor 912, a random access memory (RAM) 914, a read only memory (ROM) 916, a mouse 918, a keyboard 920 and input/output devices such as a printer 924, disk drives 922, a display 926 and a communications link 928. In other embodiments, the general purpose computer 910 may include more, less, or other component parts. Embodiments of the present disclosure may include programs that may be stored in the RAM 914, the ROM 916 or the disk drives 922 and may be executed by the processor 912 in order to carry out functions described herein. The communications link 928 may be connected to a computer network or a variety of other communicative platforms including, but not limited to, a public or private data network; a local area network (LAN); a metropolitan area network (MAN); a wide area network (WAN); a wireline or wireless network; a local, regional, or global communication network; an optical network; a satellite network; an enterprise intranet; other suitable communication links; or any combination of the preceding. Disk drives 922 may include a variety of types of storage media such as, for example, floppy disk drives, hard disk drives, CD ROM drives, DVD ROM drives, magnetic tape drives or other suitable storage media. Although this embodiment employs a plurality of disk drives 922, a single disk drive 922 may be used without departing from the scope of the disclosure.

Although FIG. 9 provides one embodiment of a computer that may be utilized with other embodiments of the disclosure, such other embodiments may additionally utilize computers other than general purpose computers as well as general purpose computers without conventional operating systems. Additionally, embodiments of the disclosure may also employ multiple general purpose computers 910 or other computers networked together in a computer network. Most commonly, multiple general purpose computers 910 or other computers may be networked through the Internet and/or in a client server network. Embodiments of the disclosure may also be used with a combination of separate computer networks each linked together by a private or a public network.

Several embodiments of the disclosure may include logic contained within a medium. In the embodiment of FIG. 9, the logic includes computer software executable on the general purpose computer 910. The medium may include the RAM 914, the ROM 916, the disk drives 922, or other mediums. In other embodiments, the logic may be contained within hardware configuration or a combination of software and hardware configurations.

The logic may also be embedded within any other suitable medium without departing from the scope of the disclosure.

It will be understood that well known processes have not been described in detail and have been omitted for brevity. Although specific steps, structures and materials may have been described, the present disclosure may not limited to these specifics, and others may substituted as is well understood by those skilled in the art, and various steps may not necessarily be performed in the sequences shown.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A wearable device comprising:
   a plurality of sensors configured to detect information concerning a wearer or a surrounding of the wearer of the wearable device, wherein at least some of the detected information is automatically communicated from the wearable device to a remote application based on:
      a request from a user of the remote application or a trigger initiated on the wearable device when the detected information from at least one of plurality of sensors indicate an event has occurred;
      wherein geolocation information of the wearable device is communicated to a portable device to allow the user of the remote application to find the wearable device; and
      wherein the geolocation information yields a compass direction of the wearable device with respect to the portable device.

2. The wearable device of claim 1, wherein the wearable device is configured to be worn around a wrist of the wearer.

3. The wearable device of claim 1, wherein the plurality of sensors include an accelerometer, a geolocation component, an audio capture component, a heart rate sensor, or a device removal sensor.

4. The wearable device of claim 1, wherein at least some of the information is continuously recorded and stored for a temporary time, and the at least some of the information that is continuously recorded and stored for a temporary time period is transmitted with the request from the user or the trigger.

5. The wearable device of claim 4, wherein the at least some of the information that is continuously recorded and stored for a temporary time is deleted after a period of time if there is no request from the user or the trigger.

6. The wearable device of claim 1, wherein the detected information from at least one of the plurality of sensors is compared to a signature to determine whether an event has occurred.

7. The wearable device of claim 6, wherein signature is dynamically updated over time to determine expected information from unexpected information.

8. The wearable device of claim 1, wherein the event is detection of an uttered request for help by the wearer of the device.

9. The wearable device of claim 8, wherein the uttered request for help is compared to a signature to distinguish requests for help from the wearer from utterances by others.

10. The wearable device of claim 1, wherein the event is a detected increase in heart rate above an expected signature.

11. The wearable device of claim 1, wherein the event is a detected distance of the wearable device being a distance away from the portable device containing the remote application.

12. The wearable device of claim 1, wherein the event is detected stress based on the information from accelerometers and at least one other sensor exceeding an expected signature.

13. The wearable device of claim 1, wherein the at least some of the detected information that is automatically communicated from the wearable device to a remote application includes audio and video.

14. The wearable device of claim 1, wherein the wearable device includes at least one movable camera, and the user of the remote application issues commands to move the camera.

15. The wearable device of claim 1, wherein the least some of the detected information is automatically communicated from the wearable device to a security or law enforcement agency.

16. The wearable device of claim 1, wherein the event is a detected removal of the wearable device.

* * * * *